United States Patent [19]

Muckerheide

[11] 4,316,467
[45] Feb. 23, 1982

[54] CONTROL FOR LASER HEMANGIOMA TREATMENT SYSTEM

[75] Inventor: Myron C. Muckerheide, Schofield, Wis.

[73] Assignee: Lorenzo P. Maun, Belleville, Ill. ; a part interest

[21] Appl. No.: 161,837

[22] Filed: Jun. 23, 1980

[51] Int. Cl.³ .............................................. A61B 17/36
[52] U.S. Cl. ........................... 128/303.1; 219/121 LB
[58] Field of Search ..................... 128/303.1, 395-398; 219/121 LA, 121 LB, 121 LZ; 331/DIG. 1

[56] References Cited

U.S. PATENT DOCUMENTS

| | | | |
|---|---|---|---|
| 3,068,739 | 12/1962 | Hicks, Jr. et al. | 128/395 X |
| 3,388,461 | 6/1968 | Lins | 219/121 LB |
| 4,072,147 | 2/1978 | Hett | 128/303.1 X |
| 4,126,136 | 11/1978 | Auth et al. | 128/303.1 |
| 4,240,431 | 12/1980 | Komiya | 128/303.1 |

FOREIGN PATENT DOCUMENTS

| | | | |
|---|---|---|---|
| 2829516 | 1/1980 | Fed. Rep. of Germany | 128/303.1 |
| 2832847 | 2/1980 | Fed. Rep. of Germany | 128/303.1 |

*Primary Examiner*—Lee S. Cohen
*Attorney, Agent, or Firm*—Wheeler, House, Fuller & Hohenfeldt

[57] ABSTRACT

A laser for directing a nominally 5 micron wavelength beam at a hemangioma or other variegated lesion. A fiber optic bundle for intercepting radiation reflected from the lesion at an intensity corresponding with the color intensity of the region at which the beam is directed. The output beam from the fiber optic bundle modulates a photodetector stage whose amplified output drives a galvanometer. The galvanometer shaft is coupled to the shaft of a potentiometer which is adjustable to regulate the laser power supply and, hence, the laser output energy level so laser beam energy is reduced when high absorption regions in the lesion are being scanned by the beam and increased as low absorption regions are being scanned.

2 Claims, 3 Drawing Figures

CONTROL FOR LASER HEMANGIOMA TREATMENT SYSTEM

This invention relates to apparatus for laser treatment of hemangiomas, commonly called portwine birthmarks or lesions, on the skin of human patients.

Inducing coagulation necrosis and eradication of a portwine mark on the skin of a patient by projecting a laser beam onto the mark is becoming a more widespread practice among plastic and reconstructive surgeons. Portwine lesions have color variations in the range of pink to dark bluish-red. Lasers such as the argon laser which produce coherent light in the blue-green part of the spectrum are usually used for treatment. The output beam from an argon laser lies in the blue-green wave length range of 4.9 to 5.1 microns as is well-known. Radiation in this wavelength range is differentially absorbed in a portwine lesion in correspondence with the degree of redness or darkness in the area increments of the lesion. When the bluish laser beam strikes a non-reddish area such as skin surrounding the hemangioma, a large amount of energy in the form of light is reflected but when the beam impinges upon deep purple or various shades of reddish purple which occur in the hemangioma, the laser light energy is heavily absorbed. Zones in the hemangioma which have been fully treated with the laser beam turn lighter or whiter than adjacent incompletely treated regions. Usually, the laser beam spot is focused to a diameter of 2 or 3 mm.

Laser beam energy in the range of 1 to 4 watts has been found suitable for treating hemangiomas and similar colored lesions. As the surgeon scans the beam spot over the lesion, various degrees of redness or darkness are encountered. When a dark zone is encountered, the surgeon wants to reduce the laser output power to avoid overtreatment since the laser energy is heavily absorbed in dark zones. Moreover, as the surgeon progresses from light to dark and dark to light zones with various shades in between, it has been necessary for the surgeon to repeatedly adjust laser power output to obtain the appropriate amount of energy for inducing necrosis but without undertreatment or overtreatment. Because the surgeon must wear highly pigmented orange protective eyeglasses to prevent the bluish argon beam from damaging his own eyes, he cannot actually see the laser beam spot although he can detect the color change in any zone that has been treated. A further problem is that the surgeon cannot adjust the laser power output indicating meter properly to the many shades of color in the lesion which can be randomly distributed. The human eye can discriminate color and shade, but cannot do so rapidly enough to enable the surgeon to make corrective adjustments of the power output of the laser as is required as the beam spot is being scanned.

SUMMARY OF THE INVENTION

An object of the present invention is to overcome the above-noted problems and inconveniences by providing for instantaneous and automatic adjustment of the laser power output inversely to the darkness or lightness of the zone on which the beam spot is impinging at any time.

Briefly stated, the laser handpiece which the surgeon uses to aim the laser beam at the lesion is coupled to the laser optical cavity by means of a fiber optic bundle which is a conventional part of the system. In accordance with the invention, however, the laser power supply is controlled with a feedback system which reduces the laser tube power output when dark zones are being impinged and increases power output for lighter zones. To achieve this objective, a fiber optic bundle is mounted on the handpiece so that its input tip intercepts light reflected from the zone at which the laser beam is directed at the time. The fiber optic bundle or light receiver conducts the reflected light to a photodetector which converts the light intensity to an electric analog signal. The output signal from the photodetector is processed in a preamplifier which increases its level. The output signal from the preamplifier is fed to another higher power amplifier whose output signal is used to drive a galvanometer. The galvanometer has an output shaft which is coupled to the shaft of a potentiometer in the laser power supply control device which potentiometer would have, heretofore, to be turned or adjusted continuously by the surgeon.

The manner in which the above-mentioned object and other more specific objects of the invention are achieved will become evident in the more detailed description of an illustrative embodiment of the invention which will now be set forth in reference to the drawing.

DESCRIPTION OF A PREFERRED EMBODIMENT

Figure 1:
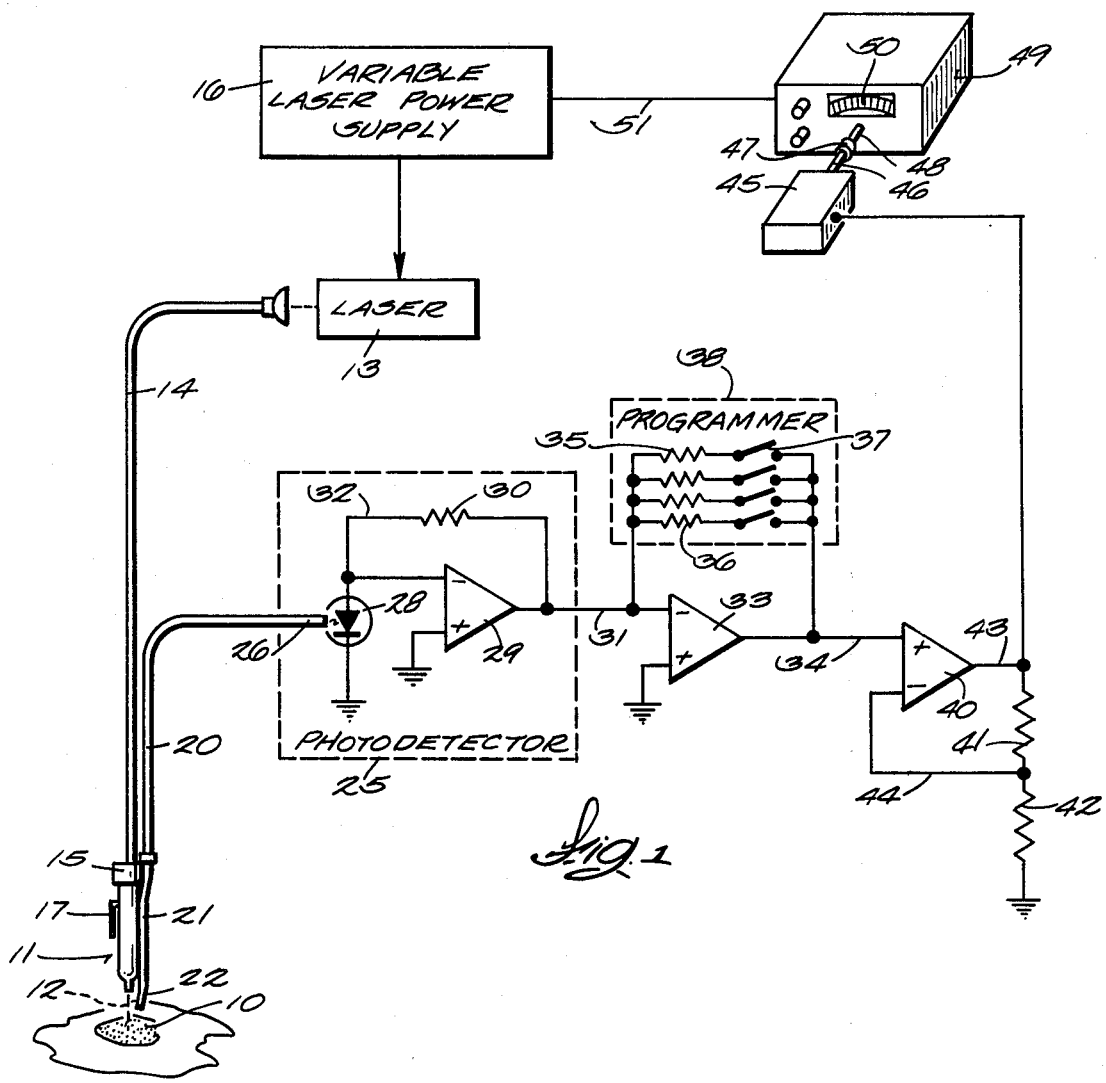
FIG. 1 is a schematic diagram of the laser hemangioma treatment system and its new automatic control.

Referring to FIG. 1, a hemangioma or other variously colored lesion on the skin of a patient is identified by the reference numeral 10. The handpiece containing the end of a fiber optic bundle from which the laser beam is projected onto the lesion is marked 11. The laser output beam is symbolized by the dashed lines 12. As indicated, it is customary to use a beam having a diameter of 2 or 3 mm for treating hemangiomas. The laser is shown symbolically and identified by the reference numeral 13. For treating hemangiomas, a laser which produces coherent radiation having a wavelength of about 5 microns is desirable. Of the presently available lasers, an argon gas laser has been found to be satisfactory. It emits radiation in a wavelength band of 4.9 to 5.1 microns.

The optical cavity of laser 13 is coupled to handpiece 11 with a fiber optic bundle 14 which terminates in the top end 15 of the handpiece. This is a known type of handpiece which has a lens, not visible, in its top end for focusing the beam of coherent laser radiation which emerges from the concealed tip of fiber optic bundle 14.

The variable power supply for laser tube 13 is represented by the block marked 16. For hemangioma treatments, the power supply is subject to being adjusted for causing the laser 13 to produce output power in the range of 0 to 4 watts. Handpiece 11 has a conventional shutter control button 17 mounted on it which, when depressed, opens the shutter, not visible, inside of the handpiece to permit the laser beam 12 to project from the handpiece.

Figure 2:
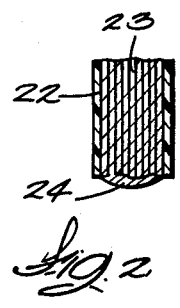
FIG. 2 is an enlargement of the tip of the fiber optic bundle which is used to conduct reflected light from the lesion being treated to the photodetector.

The system for automatically controlling the power output of the laser inversely to the degree of light absorption or reflection in the zone in the hemangioma to which the laser beam is directed comprises a fiber optic bundle 20 which extends into a tube 21 that is mounted to handpiece 11. The tip 22 of the tube and the fiber optic bundle therein is angulated as shown so it will be aligned for receiving reflected light directly from the laser light beam spot on the hemangioma 10. FIG. 2 shows an enlargement of tube tip 22 and exposes the filaments 23 of the bundle. The distal end of the bundle is fused by heating to form a convex lens 24.

Light reflected from the hemangioma 10 is conducted by way of flexible fiber optic bundle 20 to a photodetector which bears that legend and is enclosed in a dashed line rectangle marked 25. Reflected light is projected from the open end 26 of the fiber optic bundle toward a photosensor 28. The sensor should have peak sensitivity at the wavelength of the light reflected from the lesion 10 which is light at the wavelength of the argon laser 13 which is used in this example. A PIN silicon photodiode has been found suitable for argon radiation. Photodetector 25 includes an operational amplifier 29 which has a feedback resistor 30 connected between its output line 31 and its inverting input terminal 32. The output signal on amplifier output line 31 is an electric analog of the light signal which is directed to photodiode 28 for modulating its impedance.

The analog signal on line 31 is fed to an input of a preamplifier 33 which is connected as an inverting amplifier. It has a feedback loop between its output line 34 and its inverting input. The feedback loop is comprised of a plurality of resistors such as those marked 35 and 36 each of which is connected in series with a switch such as the one marked 37. Selective closure of these switches sets the gain of the laser power supply control loop to whatever reference level the surgeon deems appropriate for the nature of the particular hemangioma which is to be treated. The resistors such as 35 and switches such as 37 in the feedback circuit may be collectively designated as a programmer which is enclosed in the dashed line rectangle marked 38. A single variable resistor, not shown, could be connected between the input and output of amplifier 33 to program gain control in place of the plurality of resistors 35 and respective series connected switches 37. The reasons for providing for gain control with the programmer will be discussed in greater detail hereafter in reference to FIG. 3.

Referring again to FIG. 1, the preamplified output signal from amplifier 33 on line 34 is fed to the noninverting input of a power amplifier 40 which has a voltage divider composed of series connected resistors 41 and 42 which are connected between output line 43 of amplifier 40 and ground. The divider constitutes a feedback circuit for setting the gain of amplifier 40 by reason of the connection by way of line 44 to the midpoint of the divider.

The output signal from amplifier 40 on line 43 is conducted to a galvanometer which is not shown in detail but is represented by a box marked 45. Suitable galvanometers are commercially available and are well-known so that a description of its construction and operating mode is deemed to be unnecessary. Galvanometer 45 has a bidirectionally rotatable power output shaft 46 extending from it. This shaft will turn in one direction if the reflected light from the hemangioma is above a selected reference level and will turn in the opposite direction if the reflected light intensity is below the selected level.

Galvanometer shaft 46 is coupled by means of a coupling element 47 to the shaft 48 of a potentiometer which is concealed in a commercially available laser output control module marked 49. One of the merits of using the galvanometer to turn the laser power output potentiometer control shaft is that preexisting commercially available components can be used to implement the system. It is only necessary to remove the manual control knob, not shown, which is fastened to the potentiometer shaft 48 and use a coupling element 47 to make a mechanical connection to the output shaft 46 of the galvanometer. The illustrated commercially available control 49 is provided with a meter having a scale 50 which indicates the power output of the laser in watts. Control 49 is connected to the laser power supply 16 by means of a cable 51. The variable laser power supply 16 responds to control signals on cable 51 by increasing or decreasing the voltage applied to the laser pumping system to thereby vary laser coherent light power output correspondingly.

From the description thus far, it should be evident that when the laser beam 12 is directed to a relatively dark region in the hemangioma 10, comparatively less light will be reflected from that region to the tip of fiber optic bundle 20 in which case the photodetector will respond by decreasing the magnitude of its output signal and this decrease will be reflected through the system and result in a corresponding decrease in the output power from the laser tube to reduce the energy delivered to the relatively dark zones so that overtreatment does not result. Changing the power output from the laser in the opposite direction occurs as the laser beam is focused on lighter shades extending to almost white in which case the reflected light from the regions on the hemangioma increases and the output power from the laser increases correspondingly.

Figure 3:
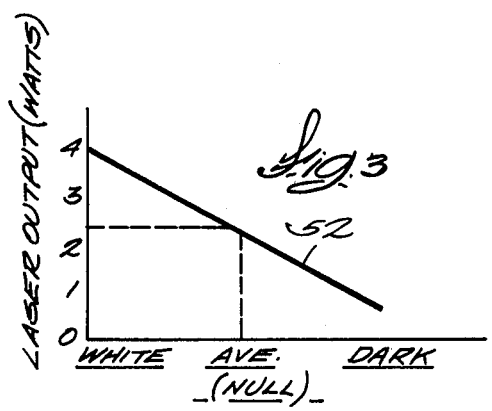
FIG. 3 is a graph showing the relationship between the color intensity of the lesion and the laser output power in watts that is obtained with the new control system.

Most surgeons will have a preference for a laser output power level which is appropriate to the technique they use in scanning the hemangioma for treatment. Each surgeon may want to set the power output level initially to substantially a skin brightness level corresponding with the lightest hemangioma region present. This may be considered a null or average condition. Then the beam can be modulated whiter than average or darker than average. The surgeon can set the average or null point by closing any of the switches such as the one marked 37 in the programmer 38. This controls the feedback, and hence, the gain of amplifer 33. Adjustment is made by selecting these switches until the desired average power is indicated on meter scale 50. A plot showing laser output in watts versus color intensity in incremental zones of the hemangioma is shown in FIG. 3 and is marked with the reference numeral 52. In this case, the average power is set for about 2.5 watts. As the fiber optic bundle and photodetector sense a lighter region, the output power automatically goes up toward a maximum of 4 watts. As darker zones are encountered, laser power output decreases for a minimum of 0.

As can be seen, the system described above provides a real time response to variations in laser energy absorption by the hemangioma on a millimeter-by-millimeter basis without ever distracting the surgeon by requiring that he repeatedly adjust the power level to avoid overtreatment or undertreatment.

Although an embodiment of the invention has been described in detail, such description is intended to be illustrative rather than limiting, for the invention may be variously embodied and is to be limited only by interpretation of the claims which follow.

I claim:

1. In a system for laser beam treatment of lesions on the body which lesions have color variations and correspondingly different coherent radiation reflection and absorption characteristics, said system comprising a laser, a power supply coupled to the laser for energizing the laser, an adjustable control for varying the output power level of the power supply and the radiation output power of the laser, a first fiber optic bundle optically coupled to the laser for conducting radiation from the laser and for directing a radiation beam onto the lesion, the improvement for automatically increasing and decreasing the radiation output power of the laser correspondingly with increasing and decreasing reflection of radiation from the lesion, comprising:

a second fiber optic bundle having radiation input and output ends, the input end adapted to be located for receiving radiation reflected from the region on which the laser beam is directed by said first fiber optic bundle within or outside of the boundaries of the lesion, photodetector means optically coupled to said output end of said second fiber optic bundle, said photodetector means being operative to produce an electric signal varying in correspondence with the intensity of the reflected radiation emitted from the output end of said second fiber optic bundle, said adjustable control for said power supply comprising a potentiometer having a shaft rotatable in opposite directions for respectively increasing and decreasing the power output from the power supply and said laser correspondingly, a galvanometer having electric signal input means and having a driven shaft, a circuit coupling said signal produced by the photodetector means to the galvanometer input means, said galvanometer responding to signals corresponding to increasing and decreasing reflection from said lesion by turning its shaft in respectively opposite directions, and means for coupling the galvanometer shaft to the potentiometer shaft such that when said galvanometer shaft turns in a direction corresponding to detection of increasing reflected radiation said potentiometer shaft turns in a direction corresponding with increasing the power output of said laser and when said galvanometer shaft turns in a direction corresponding to detection of decreasing reflected radiation said potentiometer shaft turns in a direction corresponding to decreasing the laser power output.

2. The device as in claim 1 wherein said circuit coupling said photodetector means to said galvanometer input means comprises:

amplifier means having an input and output, said signal from the photodetector means being coupled to said input and the signal from said output being coupled to said galvanometer input means, a circuit including variable resistance means connected between the input and output of said amplifier means to provide for feedback and gain control of said amplifier means by selective variation of said resistance means to thereby enable the power output of said laser to be set at an initial average level corresponding to a reference reflected radiation level.

* * * * *